United States Patent [19]

Diehl

[11] Patent Number: 5,612,026

[45] Date of Patent: Mar. 18, 1997

[54] CHOLESTEROL LOWERING DRINK MIX COMPOSITONS

[75] Inventor: Sherry L. Diehl, Cincinnati, Ohio

[73] Assignee: The Procter & Gamble Company, Cincinnati, Ohio

[21] Appl. No.: 591,840

[22] Filed: Jan. 25, 1996

[51] Int. Cl.$^6$ .................................................. A61K 31/785
[52] U.S. Cl. ........................ 424/78.01; 424/401; 426/74
[58] Field of Search ................................ 424/78.1, 78.01, 424/401; 426/74

[56] References Cited

U.S. PATENT DOCUMENTS

| | | | |
|---|---|---|---|
| 3,974,272 | 8/1976 | Polli et al. | 424/78 |
| 4,459,280 | 7/1984 | Colliupoulos et al. | 424/35 |
| 4,722,847 | 2/1988 | Heckert | 426/74 |
| 5,186,965 | 2/1993 | Fox et al. | 426/74 |
| 5,422,101 | 6/1995 | Daggy et al. | 424/78.01 |

*Primary Examiner*—Thurman K. Page
*Assistant Examiner*—Sharon Howard
*Attorney, Agent, or Firm*—Mary Catherine Poland; Douglas C. Mohl; Jacobus C. Rasser

[57] ABSTRACT

Disclosed are drink mix compositions comprising a therapeutically effective dose of an anion exchange resin, xanthan gum, and an edible, water soluble salt at a level wherein the gelation rate of the drink mix compositions in a aqueous solution is reduced. These compositions may also contain one or more carriers wherein the compositions are in a form mixable with a liquid to form a suspension of the anion exchange resin, xanthan gum, and edible, water soluble salt.

16 Claims, No Drawings

CHOLESTEROL LOWERING DRINK MIX COMPOSITONS

BACKGROUND OF THE INVENTION

High blood cholesterol levels are associated with life threatening cardiovascular diseases. Cholestyramine and colestipol hydrochloride are drugs used in treating hypercholesterolemia. These drugs are known as basic anion exchange resins. They help to lower blood cholesterol levels apparently by binding to bile acids in the intestine. It is believed that this in turn causes an increase in hepatic metabolism of cholesterol to replenish the bile acids lost to complexation with the anion exchange resins.

Cholestyramine is usually dosed at four grams (anhydrous weight), one to six times daily. At the present time cholestyramine is commercially available as Questran® and Questran® Light (manufactured by the Bristol-Myers Squibb Company) in a four gram unit dose powder packet or in bulk powder. [*Physicians Desk Reference*, 49th Edition, pages 735–739 (1995).] Cholestyramine is commercially available as Duolite AP-143 resin (Rohm & Haas Co.).

Colestipol hydrochloride is usually administered at five to thirty grams daily given once or in divided doses. Colestipol hydrochloride is commercially available under the tradename Colestid® (colestipol hydrochloride granules, manufactured by The Upjohn Company). It is sold in a five gram unit dose powder packet or in bulk powder. [*Physicians Desk Reference*, 49th Edition, pages 2531–2534 (1995)].

While the benefits of anion exchange resins are well known and appreciated, the aesthetics (e.g., mouthfeel, taste, and throat sticking) are considered by many users to be very unacceptable. The unpleasant mouthfeel of cholestyramine is frequently described as a sandy, gritty texture which tends to stick to the back of the mouth and throat upon ingestion and which leaves an unpleasant fishy taste in the mouth. Colestipol hydrochloride is described as having an astringent taste and a sandy, gritty texture which sticks to the mouth and teeth after ingestion. Obviously, poor aesthetics raise concern about how closely patients will comply with any treatment regimen using these agents.

Research has been done in an effort to improve the palatability of anion exchange resins. Patents which disclose such efforts include: French Medical Patent 6,888 M published Jun. 4, 1964 by Mead Johnson & Company which describes dry mixing acacia gum with cholestyramine resin to aid in making the astringency of cholestyramine disappear; and U.S. Pat. No. 3,974,272 to Polli et al., issued Aug. 10, 1976 which describes a palatable oral coacervate composition containing cholestyramine and a modified gum selected from hydrophilic colloid of cellulosic material and charged anionic gum in an aqueous medium.

Despite the research aimed at improving the compositions containing anion exchange resins, a great need still exists for compositions that provide therapeutic benefit while maintaining an agreeable texture and taste, thereby encouraging patient compliance with the treatment regimen. It has been discovered in the present invention that combining an anion exchange resin, such as cholestyramine or colestipol hydrochloride, with xanthan gum and an edible, water soluble salt aids in masking the unpleasant taste and mouthfeel associated with these resins. It has also been discovered that such compositions can be formulated as aesthetically pleasing drink mix compositions. It has further been discovered that the gelation rate of xanthan gum/anion exchange resin-containing compositions may be reduced by the addition of an edible, water soluble salt. This reduction in gelation rate has the advantage of further enhancing the aesthetics of an anion exchange resin therapeutic regimen.

These and other objects of the present invention will become readily apparent from the detailed description which follows. All percentages and ratios used herein are by weight unless otherwise specified. Screen mesh sizes used herein are based on U.S. standards. The abbreviation "g", as used herein refers to "grams".

SUMMARY OF THE INVENTION

The present invention relates to a drink mix composition comprising a therapeutically effective dose of an anion exchange resin; from about 0.05 g to about 1.25 g of xanthan gum; and from about 0.3 g to about 1.75 g of edible, water soluble salt at a level wherein the gelation rate of the drink mix composition in an aqueous solution is reduced; and wherein further the compositions are in a form mixable with a liquid to form a suspension of the anion exchange resin, xanthan gum and edible, water soluble salt.

DETAILED DESCRIPTION OF THE INVENTION

The drink mix compositions of the present invention are compositions useful for reducing serum cholesterol levels containing an anion exchange resin, xanthan gum and an edible, water soluble salt. Such composition may be in any form suitable for mixing with a liquid to form an anion exchange resin/xanthan gum/edible, water soluble salt suspension for oral consumption. Preferred form is a dry powder in bulk or unit dose form which readily mixes and disperses in a liquid. Suitable liquids include any liquid suitable for human consumption such as water, juices, milk or other liquids.

The levels of xanthan gum and edible, water soluble salts disclosed herein are based on a preferred therapeutically effective dose of anion exchange resin (i.e., 4 g anhydrous weight per dose of cholestyramine or 5 g per dose of colestipol hydrochloride) in 6 ounces of a liquid. Also included in the present invention are compositions which vary in delivered dose of anion exchange resin or amount of liquid or both. Such compositions may be formulated by varying the level of components in proportion to the levels of components disclosed herein.

The essential and optional components of the compositions according to the present invention, and representative amounts, are described in detail as follows.

Xanthan Gum

The present drink mix compositions contain xanthan gum. Xanthan gum is a polysaccharide gum produce by the bacterium *Xathomonas compestris*. Xanthan gum is a cream-colored, free-flowing, odorless powder which dissolves in water to provide highly viscous solutions at low concentrations. The *Merck Index*, Tenth Edition, published by Merck & Co., No. 9868, (1983). Xanthan gum is available commercially under the tradename Keltrol®, by the Kelco Division of Monsanto & Co., San Diego Calif. Keltrol® is available in various particles sizes such as Keltrol® F (fine grade of xanthan gum), and Keltrol® 1000. All such xanthan gum formulations are considered suitable for use in the present invention, however the amount of xanthan gum utilized may vary depending on the particle size. For example, a smaller amount of a fine grade xanthan gum will be needed in the present compositions, in comparison to a coarser grade, due to the greater surface area of the small particles.

Xanthan gum, utilizing a grade such as Keltrol® 1000, may be used in the present compositions at a level of from about 0.4 g to about 1.25 g, preferably from about 0.5 g to about 1.1 g, and most preferably from about 0.75 g to about 0.95 g. A finer grade of xanthan gum such as Keltrol® F, may be used at a level of from about 0.05 g to about 0.5 g, preferably from about 0.1 g to about 0.35 g, and most preferably from about 0.15 g to about 0.25 g.

Anion Exchange Resin:

The term "anion exchange resin", as used herein, means any resinous material having cationic moieties such that the material is safe and therapeutically effective for treating hypercholesterolemia (at a reasonable benefit/risk ratio within the scope of sound medical judgment). Preferred anion exchange resins useful herein include cholestyramine, colestipol hydrochloride, or others containing quaternary ammonium groups.

Cholestyramine is a strongly basic anion exchange resin which contains quaternary ammonium functional groups attached to a styrene-divinylbenzene copolymer. [*The Merck Index*, 10th Edition, published by Merck & Co., No. 2182 (1983), incorporated by reference herein in its entirety].

Colestipol hydrochloride is an insoluble, high molecular weight basic anion-exchange copolymer of diethylene triamine and 1-chloro-2,3-expoxypropane with approximately 1 out of 5 amine nitrogen's protonated (chloride form). [*The Merck Index*, 11th edition, published by Merck & Co., No. 2472 (1989), incorporated by reference herein in its entirety].

The present compositions comprise a therapeutically effective dose of the anion exchange resin. The term "therapeutically effective amount", as used herein, means an amount of the anion exchange resin which is clinically recognized for treating hypercholesterolemia. Such amounts or dosing may vary depending on the anion exchange resin used. For example, presently the generally recognized therapeutically effective amount is about 4 g anhydrous weight per dose of cholestyramine, and about 5 g per dose of colestipol hydrochloride.

Edible, Water Soluble Salts:

The term "edible, water soluble salts" as used herein, means any salt material, organic or inorganic, which is soluble in water (under normal use conditions for an anion exchange resin-containing drink mix composition) and which is safe for ingestion by humans. Examples of edible, water soluble salts include magnesium sulfate, calcium chloride, calcium sulfate, calcium citrate malate, potassium chloride, sodium chloride, potassium sulfate, sodium sulfate, zinc chloride, zinc sulfate, potassium sorbate, and mixtures thereof. Preferred are the salts of divalent cations (e.g. calcium, magnesium, zinc) and especially those salts of strong inorganic acids (e.g., magnesium sulfate, calcium sulfate, calcium chloride, zinc sulfate, zinc chloride, and mixtures thereof). The present compositions may also comprise one or more of the edible water soluble salts.

As used herein, the term "calcium citrate malate" refers to a mixture or (preferably) a complex of calcium, citrate and malate. The calcium citrate malate may consist of a mixture of calcium citrate and calcium malate, a complex of calcium containing citrate and malate ligands, a mixture of a calcium salt with citric acid and malic acid, or combinations thereof. Calcium citrate malate is a highly bioavailable source of calcium. Calcium citrate realate for use herein may be preformed as a powder or can be formed in situ. Preferred calcium citrate malate have calcium:citrate:malate molar ratios of about 6:2:3 and 4:2:3. Methods for making calcium citrate malate are described in the following documents, incorporated by reference herein in their entirety: Japanese Patent Specification SHO 56-97248, Kawai, published Aug. 5, 1981; U.S. Pat. No. 4,722,847, issued to Heckert, Feb. 2, 1988; and U.S. Pat. No. 5,186,965, issued to Fox et al., Feb. 16, 1993.

It is necessary for the purposes of the present invention for the amount of the edible, water soluble salt to be present in an amount sufficient to reduce the gelation rate of the drink mix composition relative to the compositions without the added salt. This is especially important for salts of certain organic acids which at certain levels can have the unwanted effect of increasing the gelation rate of xanthan gum alone suspensions (i.e., make the solution thicker, faster), but when used at other levels may provide the desired benefit of reducing the gelation rate according to the present invention.

Determination of whether the level of salt present in the xanthan gum/anion exchange resin-containing composition is at a level wherein the gelation rate of the edible, water soluble salt/xanthan gum/anion exchange resin-containing drink mix composition in an aqueous solution is reduced, as required by the present invention, is readily made by simple experimentation. For example, it is possible to compare the rate of viscosity increase for a composition containing the salt versus the composition containing the same components but not the edible, water soluble salt. If the rate of gelation is slowed by the addition of the amount of salt used, a sufficient level of the salt(s) as taught by the present invention is present. Methods and equipment for measuring gelation rates and viscosity of liquids are known, such as the Brookfield Viscometer. Such measurements and determinations can easily be made by one skilled in the art. Compositions of the present invention therefore may comprise from about 0.3 g to about 1.75 g edible, water soluble salts, preferably from about 0.4 g to about 1.5 g, and more preferably from about 0.5 g to about 1.25 g.

Carriers

The present invention may optionally contain one or more carriers. Suitable carriers must be safe for oral administration to humans, and may be chosen by one of ordinary skill in the art as appropriate for the drink mix form and use intended for the product.

Suitable carriers herein, depending on desired properties and intended end use, are selected from the group consisting of suspending agents, solubilizing agents, diluents, surfactants, buffers, lubricants, thickeners, agglomerating materials, fillers, extenders, emulsifiers, flavoring agents, coloring agents, humectants, edible acids, sweetening agents, binders, disintegrating agents, flow-inducing agents, plasticizers, wetting agents, antioxidants, stabilizers and other additives. One or more of the carriers may be added to the present anion exchange resin/xanthan gum/edible, water soluble salt drink mix compositions .in quantities sufficient to achieve desired formulation characteristics according to the formulator's preference.

Most preferred are products of the present invention in dry powder form suitable for mixing in a liquid to form a edible, water soluble salt/xanthan gum/anion exchange resin-containing drink. Preferred carriers for such powder forms are known and are also described in detail, for example, in U.S. Pat. Nos. 4,459,280 and 4,548,806, incorporated hereinbefore by reference. Preferred are such powders comprising maltodextrin. The compositions of the present invention may be prepared by dry blending the components. Such dry blending techniques are well-known in the art such as Ribbon mixers, V-blenders, Paddle mixers, Nauta mixers, Tote mixers, and Forberg mixers.

It is preferred that the compositions of the present invention be prepared by agglomeration and/or other means of composition coating for improved aesthetics and mixing. In the present invention, suitable techniques for agglomeration include any technique well-known in the art, such as fluid bed agglomeration. Preferred are agglomerates of xanthan gum and/or coated xanthan gum, especially agglomerated with maltodextrin and/or sucrose. However, agglomerates of xanthan gum may also include one or more of an edible acid, sweetening agents, coloring agents, dietary fibers. Also, some or all of the edible, water soluble salt and/or anion exchange resin may also be included.

Agglomerating materials preferred for use herein are known. These agglomerating materials include those selected from the group consisting of water dispersible hydrolyzed starch oligosaccharide, mono-saccharide, di-saccharide, polyglucose, polymaltose, polyvinyl pyrrolidone, and mixtures thereof.

The present compositions may optionally comprise an edible acid. The term "edible acids", as used herein, means any water soluble acid material having a $pK_a$ of less than about 5, preferably within the range of from about 2 to about 5, and is safe for ingestion by humans. Examples of edible acids include, but are not limited to, citric acid, ascorbic acid, malic acid, succinic acid, tartaric acid, phosphoric acid, monopotassium phosphate and mixtures thereof. Preferred are ascorbic acid, phosphoric acid, malic acid, and citric acid, with citric acid being most preferred. Preferred compositions of the present invention are those which have some or all of the edible acid coated on the xanthan gum.

The present compositions may optionally contain one or more sweetening agents. Suitable sweetening agents include saccharides, disaccharides and polysaccharides such as xylose, ribose, glucose, mannose, galactose, fructose, dextrose, sucrose, maltose, partially hydrolyzed starch or corn syrup solids and sugar alcohols. Sugar components also include materials such as invert sugar syrups, brown sugar, honey, molasses, maple syrups and the like.

Artificial sweetening agents may also be included. Such agents include aspartame, saccharin, cyclamate, acesulfame, gem sweet, L-sugars, trichloro sucrose, aspartyl-D-valine, glycyrrhizin, p-phenetylurea, and neohesperidin hydrochalcone. Preferred artificial sweeteners are saccharin, cyclamate, acesulfame K, and aspartame, sold as Nutrasweet® By G. D. Searle.

One or more flavoring agents may also be included. Such agents may be volatile oils, liquids or dry agents which are pharmaceutically acceptable for internal ingestion by humans. Examples of flavoring agents include but are not limited to citrus flavors such as orange and grapefruit; strawberry; cherry; apricot; banana; chocolate; vanilla and vanilla cream; mint flavors such as peppermint and spearmint; spices such as cinnamon, clove and nutmeg; and nut flavors such as hazelnut, peanut butter and almond.

Dietary fibers may also be included as optional carriers. Preferred is psyllium husk fiber but other dietary fibers such as cellulose derivatives (i.e., methylcellulose, hydroxypropylmethyl cellulose, and hydroxypropyl cellulose), and cereal brans such as wheat, corn, barley, rye, oats, rice, and soybean may also be used.

The present compositions may also include a humectant which provides the benefit of a mixing agent. Preferred is glycerin, which is commercially available in food grade quality.

The present compositions may also optionally comprise other additives which include milk products such as whole milk, skim milk, whey, various milk powders, egg products, other protein sources such as soy protein, preservatives such as sorbic acid, polyhydric alcohols such as glycerol and propylene glycol, emulsifiers such as lecithin, modified celluloses, antioxidants such as ascorbic acid, and coloring agents and dyes.

Method of Treatment:

The method of treatment herein comprises orally administering to a human or lower animal patient in need of having a lowered blood cholesterol level a safe and effective amount of an aqueous liquid suspension of a edible, water soluble salt/xanthan gum/anion exchange resin-containing composition according to the present invention. The term "safe and effective amount", as used herein, means an amount of the drink mix composition high enough to significantly positively modify the hypercholesterolemic condition being treated, but low enough to avoid serious side effects (at a reasonable benefit/risk ratio), within the scope of sound medical judgment. The safe and effective amount will vary with the age and physical condition of the patient being treated, the nature of the condition, the duration of treatment, the nature of concurrent therapy, and like factors within the knowledge and expertise of the attending physician. However, a patient in need of such treatment will typically receive about 4 g to about 24 g daily of the cholestyramine, or from about 5 g to about 30 g daily of the colestipol hydrochloride. The following examples further describe and demonstrate embodiments within the scope of the present invention. These examples are given solely for the purpose of illustration and are not to be construed as limitations of the present inventions as many variations thereof are possible without departing from the spirit and scope.

EXAMPLE 1

| Components | Grams/dose |
| --- | --- |
| Cholestyramine[a] | 4.400 |
| Maltodextrin, NF[b] | 0.650 |
| Xanthan Gum, NF[c] | 0.850 |
| Magnesium Sulfate heptahydrate, USP | 0.600 |
| Citric Acid, USP (anhydrous, fine) | 0.250 |
| Orange Flavor | 0.600 |
| Vanilla Cream Flavor | 0.040 |
| Aspartame | 0.060 |
| D&C Yellow #10 | 0.004 |
| FD&C Yellow #6 | 0.002 |

[a] equal to about 4 g anhydrous weight
[b] Maltrin M100 sold by Grain Processing Inc., (Muscatine, Iowa)
[c] Keltrol® 1000 sold by the Kelco Division of Monsanto & Co., (San Diego, California).

Prepare Example 1 using wet agglomeration and granulation as follows: charge cholestyramine, xanthan gum and maltodextrin to a fluid bed dryer such as Glatt, and allow to mix. Form a binder solution of water and magnesium sulfate. Spray binder solution on cholestyramine mix to form agglomerates/granules. Note: other ingredients such as citric acid, dyes, etc. can be added to the binder solution, but process cycle time may increase. Dry agglomerates to desired moisture content (e.g. loss on drying equals about 5–10%). Dry blend remainder of ingredients after drying. The dose weight of the composition in Example 1 is about 7.46 g. The 7.46 g of the composition in Example 1 is dispersed in 6 ounces of water and then consumed by a person in need of treatment for hypercholesterolemia, delivering about 4 g per dose of cholestyramine.

EXAMPLE 2

| Components | Grams/dose |
| --- | --- |
| Aspartame | 0.0510 |
| Citric Acid | 0.2980 |
| D&C Yellow #10 | 0.0040 |
| Cholestyramine[a] | 4.4740 |
| Calcium Carbonate | 0.0430 |
| Malic Acid | 0.0850 |
| Sodium Citrate | 0.1700 |
| Magnesium Sulfate | 0.5100 |
| Xanthan Gum[b] | 0.2000 |
| FD&C Yellow #6 | 0.0030 |
| Orange Flavor | 0.4680 |
| Vanilla Cream | 0.0340 |

[a]equals about 4 g anhydrous weight
[b]Keltrol® F sold by the Kelco Division of Monsanto & Co., (San Diego, California)

Prepare Example 2 in dry mix form by blending all powders in a mixer with no other processing steps. A ribbon blender, paddle mixer, V-blender or other comparable mixer may be used. The dose weight of the composition in Example 2 is about 6.3400 g. The 6.3400 g of the composition in Example 2 may be dispersed in 6 ounces of water and then consumed by a person in need of treatment for hypercholesterolemia, delivering about 4 g of cholestyramine.

EXAMPLE 3

| Components | Grams/dose |
| --- | --- |
| Aspartame | 0.0600 |
| Calcium Carbonate | 0.0500 |
| Colestipol Hydrochloride | 5.0000 |
| Xanthan Gum[a] | 0.2 |
| Citric Acid | 0.3500 |
| D&C Yellow #10 | 0.0050 |
| FD&C Yellow #6 | 0.0030 |
| Malic Acid | 0.1000 |
| Orange Flavor | 0.5500 |
| Magnesium Sulfate | 0.6000 |
| Sodium Citrate | 0.2000 |
| Vanilla Cream | 0.0400 |

[a]Keltrol® F, sold by Kelco Division of Monsanto & Co. (San Diego, California)

Prepare Example 3 by adding aspartame, citric acid, calcium carbonate, malic acid, orange flavor, magnesium sulfate, vanilla flavor, sodium citrate, FD &C Yellow #6 and #10 in a Hobart bowl and mixing for 4 minutes using speed #1. Next add colestipol hydrochloride and xanthan gum and mix for 5 minutes or until uniform. The dose weight of the composition in Example 3 is about 7.16 g. The 7.16 g of the composition in Example 3 may be dispersed in 6 ounces of water and then consumed by a person in need of treatment for hypercholesterolemia, delivering about 5 g of colestipol hydrochloride.

What is claimed is:

1. A drink mix composition comprising:
   (a) a therapeutically effective dose of an anion exchange resin;
   (b) from about 0.05 g to about 1.25 g of xanthan gum; and
   (c) from about 0.3 g to about 1.75 g of edible, water soluble salt at a level wherein the gelation rate of the drink mix composition in an aqueous solution is reduced.

2. The composition according to claim 1 wherein the edible, water soluble salt is selected from the group consisting of magnesium sulfate, calcium chloride, calcium sulfate, calcium citrate malate, potassium chloride, sodium chloride, potassium sulfate, sodium sulfate, zinc chloride, zinc sulfate, potassium sorbate, and mixtures thereof.

3. The composition according to claim 1 wherein the anion exchange resin is cholestyramine.

4. The composition according to claim 3 where the xanthan gum is a small particle size xanthan gum used in an amount of from about 0.05 g to about 0.5 g.

5. A drink mix composition comprising:
   (a) a therapeutically effective dose of an anion exchange resin;
   (b) from about 0.05 g to about 1.25 g of xanthan gum;
   (c) from about 0.3 g to about 1.75 g of edible, water soluble salt at a level wherein the gelation rate of the drink mix composition in an aqueous solution is reduced; and
   (d) one or more carriers;
   and wherein further the composition is in a form mixable with a liquid to form a suspension of the anion exchange resin, xanthan gum and edible, water soluble salt.

6. The composition according to claim 5 wherein the edible, water soluble salt is selected from the group consisting of magnesium sulfate, calcium chloride, calcium sulfate, calcium citrate malate, potassium chloride, sodium chloride, potassium sulfate, sodium sulfate, zinc chloride, zinc sulfate, potassium sorbate, and mixtures thereof.

7. The composition according to claim 6 wherein the drink mix composition is prepared by dry mixing.

8. The composition according to claim 7 where the xanthan gum is a small particle size xanthan gum used in an amount of from about 0.05 g to about 0.5 g.

9. A drink mix composition comprising:
   (a) a therapeutically effective dose of cholestyramine;
   (b) from about 0.05 g to about 1.25 g of xanthan gum;
   (c) from about 0.3 g to about 1.75 g of magnesium sulfate wherein the gelation rate of the drink mix composition in an aqueous solution is reduced; and
   (d) one or more carriers;
   and wherein further the composition is in a form mixable with a liquid to form a suspension of the cholestyramine, xanthan gum and magnesium sulfate.

10. The composition according to claim 9 wherein the drink mix composition is prepared by agglomeration.

11. The composition according to claim 10 wherein the carriers comprise an edible acid, agglomerating materials, a sweetening agent, one or more coloring agents, and one or more flavoring agents.

12. The composition according to claim 11 wherein the edible acid is selected from the group consisting of citric acid, phosphoric acid, and mixtures thereof.

13. The composition according to claim 12 where the xanthan gum is a small particle size xanthan gum used in an amount of from about 0.05 g to about 0.5 g.

14. A method for reducing serum cholesterol levels in humans or lower animals, said method comprising orally administering to a human or lower animal in need of such treatment a safe and effective amount of the drink mix composition according to claim 1.

15. A method for reducing serum cholesterol levels in humans or lower animals, said method comprising orally administering to a human or lower animal in need of such treatment a safe and effective amount of the drink mix composition according to claim 5.

16. A method for reducing serum cholesterol levels in humans or lower animals, said method comprising orally administering to a human or lower animal in need of such treatment a safe and effective amount of the drink mix composition according to claim 9.

* * * * *